(12) United States Patent
Becker et al.

(10) Patent No.: US 10,037,678 B2
(45) Date of Patent: Jul. 31, 2018

(54) SYSTEM AND METHOD FOR PROVIDING A PERSONALIZED WASHROOM EXPERIENCE TO PATRONS

(71) Applicant: Kimberly-Clark Worldwide, Inc., Neenah, WI (US)

(72) Inventors: Stephen Becker, Cumming, GA (US); Charlene Dunbar, Liburn, GA (US); Jason Kirkland, Cumming, GA (US); Warren Moede, Atlanta, GA (US); Tom Schulz, Roswell, GA (US); Chrissy Sheehan, Media, PA (US); Peter W. Shipp, Jr., Woodstock, GA (US); Matt Zielinski, Darien, CT (US); Paul F. Tramontina, Harleysville, PA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 15/544,567

(22) PCT Filed: Jan. 30, 2015

(86) PCT No.: PCT/US2015/013878
§ 371 (c)(1),
(2) Date: Jul. 19, 2017

(87) PCT Pub. No.: WO2016/122628
PCT Pub. Date: Aug. 4, 2016

(65) Prior Publication Data
US 2017/0372589 A1 Dec. 28, 2017

(51) Int. Cl.
*G08B 21/22* (2006.01)
*G08B 21/24* (2006.01)
*G06F 19/00* (2018.01)
*G08B 7/06* (2006.01)
*G06Q 10/10* (2012.01)
*G16H 10/60* (2018.01)

(52) U.S. Cl.
CPC .......... *G08B 21/22* (2013.01); *G06F 19/322* (2013.01); *G06Q 10/1095* (2013.01); *G08B 7/06* (2013.01);
(Continued)

(58) Field of Classification Search
CPC .......... G06K 19/0723; G06K 7/10366; G06K 7/0008; G06K 19/07749; G06K 7/10297; G06K 2017/0051; G06K 7/10158
(Continued)

(56) References Cited

U.S. PATENT DOCUMENTS

| 4,896,144 A | 1/1990 | Bogstad |
| 2006/0067545 A1 | 3/2006 | Lewis et al. |

(Continued)

FOREIGN PATENT DOCUMENTS

| CN | 1776727 A | 5/2006 |
| CN | 103218728 A | 7/2013 |

(Continued)

OTHER PUBLICATIONS

PCT Search Report, dated Oct. 27, 2015.

*Primary Examiner* — Mark Blouin
(74) *Attorney, Agent, or Firm* — Dority & Manning, P.A.

(57) ABSTRACT

A washroom system and related operations method are provided wherein patrons receive a personalized message or other personalized washroom experience. A washroom facility is configured with a receiver that receives a respective ID signal unique to particular patrons that enter the facility. The unique ID signal is transmitted by a device carried by the patrons. A processor system is in communication with the receiver for receipt of the unique ID signals. The processor system includes a memory with a file associated with each of the unique ID signals, the files containing information on the respective patron associated with the unique ID signal (Continued)

that is retrieved by the processor and used to generate and transmit the personalized message to a broadcast device in the washroom facility.

14 Claims, 5 Drawing Sheets

(52) U.S. Cl.
CPC ........... *G08B 21/24* (2013.01); *G08B 21/245* (2013.01); *G16H 10/60* (2018.01)

(58) Field of Classification Search
USPC ...................................................... 340/10.42
See application file for complete search history.

(56) References Cited

U.S. PATENT DOCUMENTS

| | | | |
|---|---|---|---|
| 2006/0105751 A1 | 5/2006 | Bloom | |
| 2011/0260872 A1 | 10/2011 | Kennish | |
| 2012/0062382 A1* | 3/2012 | Taneff | G06F 19/327 340/573.1 |
| 2013/0124247 A1* | 5/2013 | Yenni | G06Q 10/06 705/7.15 |
| 2013/0132172 A1 | 5/2013 | Liu et al. | |

FOREIGN PATENT DOCUMENTS

| | | |
|---|---|---|
| KR | 10-2012-0132883 A | 12/2012 |
| KR | 10-1225366 B1 | 2/2013 |

\* cited by examiner

SYSTEM AND METHOD FOR PROVIDING A PERSONALIZED WASHROOM EXPERIENCE TO PATRONS

FIELD OF THE INVENTION

The present invention relates generally to public or semi-private washrooms, such as public restrooms, wherein patrons are detected upon entry into the washroom facility and a message is automatically generated and displayed or played for the patron.

BACKGROUND

Washroom detection systems have been proposed wherein patrons are detected upon entry into a public or semi-private washroom facility, for example by various detection systems, including motion sensors, mechanical door sensors, infra-red sensors, and the like, and a message is automatically generated and provided to the patron. For example, U.S. Pat. No. 4,896,144 describes a warning system adapted to warn someone to wash their hands prior to leaving or entering a facility in which hand washing is important. The system includes a door activated mechanism that can be either visible or audible, and can include a door locking system and a remote signaling system. The warning system is armed when the door is opened to permit entry into the facility and is de-activated upon the actuation of hand-washing facilities.

U.S. Pub. No. US 2006/0067545 A1 describes a device to encourage hand washing compliance in a facility such as a washroom, the device including a housing configured for detachably mounting on a support surface. An ambient light sensor is disposed relative to the housing to detect ambient light within the room. An audio device within the housing contains at least one audible hand washing compliance message track that is played over a speaker within the housing. A controller is in operable communication with the ambient light sensor and the audio device, and activates the device upon determining whether a threshold amount of ambient light is present in the room.

The proposed described above are impersonal in that they issue the same generic message to all patrons. Eventually, the messages become mundane to the public and loose effectiveness. Some may even consider the impersonal messages to be an annoyance, and may ignore the messages altogether.

The present invention provides a system and methodology wherein any manner of washroom message is personalized and provided to the respective individual patron upon detection of the individual in the washroom. Because such messages are addressed to the individual, and may include personalized information or greetings, the messages will catch the individual's attention and will likely be listened and adhered to.

SUMMARY OF THE INVENTION

Objects and advantages of the invention will be set forth in part in the following description, or may be obvious from the description, or may be learned through practice of the invention.

A washroom system is presented incorporating aspects of the invention. The term "washroom" is used generically herein to encompass any manner of public, semi-public, or private facility visited by patrons to use sink or toilet facilities, bathing facilities, changing facilities, and so forth. Such facilities are also known as restrooms, toilet closets, public bathrooms, men's room, ladies' room, and the like. A typical public or semi-private washroom has a number of toilet facilities or urinals and sinks.

Although the present washroom system is particularly useful in an "away-from-home" public or semi-private environment, the system is not limited by scope of use. As used herein, the term "away-from-home" means a place or location where people congregate for various reasons or purposes that are outside the typical home. Examples of away-from-home locations include places of business, such as office buildings, office suites, retail stores, and warehouses, manufacturing facilities; schools; hospitals and other types of medical facilities; places of worship; hotels and motels; conference centers; and the like. The system is particularly useful in structures wherein multiple washroom facilities are provided for use of the building tenants or an industrial or manufacturing site wherein multiple site facilities are provided for a controlled populace. It should be appreciated though that the present washroom system may prove useful in a residential or private environment, and such uses are within the scope and spirit of the invention.

The washroom system includes a washroom facility configured with one or more receivers that receive a respective ID signal unique to particular patrons that enter the facility. In this regard, an ID signal transmitter is carried by the respective patrons, with each of the ID signal transmitters generating an ID signal that is unique to the respective patron. A computer processor system is in wired or wireless communication with the receiver, wherein the receiver transmits the unique ID signals to the processor system. The processor system includes a memory with files associated with each of the unique ID signals, wherein the files contain information unique to the patron associated with the unique ID signal. The file information is retrieved by the processor and used to generate and transmit a personalized message to a broadcast device in the washroom facility for viewing or listening by the patron. The personalized message identifies the respective patron by name and provides a greeting, information or instruction to the patron. For example, the patron may be provided with an audio or visual message such as, "Good morning John, please remember to wash your hands."

In a particular embodiment, the stored files contain preferences of the respective patron, and the additional information or instructions may relate to subject matter of preferences. For example, the patron may have previously submitted a preference profile that contains their favorite sports teams, stock quotes, hobbies, and so forth. Upon entering the washroom facility, the patron may be provided with a message such as, "Good morning John, good news, the Packers beat the Colts yesterday 17 to 10 in overtime", or "Good afternoon John, ATT stock is up 2.5 points today."

In another embodiment, the stored files may contain pre-authorized medical information of the respective patron, and the additional information or instruction in the personalized message relates to the medical information. For example, the patron may be provided with a message such as, "Good morning Lisa, please remember to take your medication at lunch today."

The personalized message may convey general health or well-being information and suggestions. For example, such message may encourage the patron by name to exercise at least one-half hour that day, or inform the patron of exercise class schedules at an on-site facility. During summer months, the message may encourage patrons to wear sunscreen, and so forth. The type of health information that may be conveyed to the patrons is vast.

In still another embodiment, the processor system may be linked to an electronic calendar for the respective patron, and the additional information or instruction relates to upcoming events on the patron's calendar. For example, the patron may be provided with a message such as, "Good morning Ellen, your next appointment is a teleconference at 3:00 pm today."

It should be appreciated that the present washroom system is not limited by the type or scope of personalized message delivered to the patrons of the washroom facility.

The processor system may be variously configured with hardware and software to carry out the functions provided for herein. For example, the processor system may be linked to a news or current events service, such as news, sports, or financial websites, and configured to generate real-time personalized messages reflecting the patrons' preferences, as discussed above.

In another less-complicated system, the processor system may include a library of generic messages, such as "Good morning _____" or "Have a nice day _____, please remember to wash your hands." The processor retrieves any one or combination of the generic messages and personalizes such messages with the information unique to the respective patron to generate the personalized message to the patron (e.g., by inserting the patron's name in the blanks).

In yet another embodiment, the washroom facility is a "smart" facility wherein the functional locations (e.g., sinks, toilets, changing closets, etc.) are remotely monitored as to availability or operational status. For example, toilet stalls in the facility may be provided with any manner of suitable detector that detects the presence of a person at the location, and transmits such information to a central monitoring station. The processor system may be linked to this central monitoring station, and the personalized message to the patron may include information or instruction relating to the status or availability of functional locations within the washroom facility. For example, the patron may be provided with a message such as, "Good evening John, stall number 4 is not in service. Stalls 1 through 3 are vacant."

The processor system may be located in the washroom facility, for example in a control cabinet within the facility, or may be remote from the facility. For example, in an office building wherein one or more smart washroom facilities are provided on each floor, the processor system may be in a centralized remote location that also serves as the monitoring station for all of the facilities. The processor system may be integrated with the monitoring station central computer system, and may be common to the plurality of washroom facilities via any suitable wired or wireless communication protocol.

Although a number of different transmitter/receiver technologies may be configured for the present washroom system, in a particular embodiment, the ID signal transmitter is a Bluetooth Low Energy (BTLE) beacon that emits a unique BTLE ID signal for each respective patron. The receiver is a BTLE-enabled receiver that receives and transmits all or a portion of the unique BTLE ID signals to the processor system, which enables the processor system to retrieve the file associated with the BTLE ID signal an generate one or more of the personalized messages for playback to the patron. The BTLE beacon may be incorporated with a device that is provided to the patrons, such as a trinket, badge, bracelet, and so forth. Alternatively, the BTLE beacon may be incorporated with a mobile smart device carried by the patron, wherein the mobile smart device runs an application that causes the mobile smart device to transmit the unique BTLE ID signal.

The broadcast device within the washroom facility may be any one or combination of an audio device, video device, or audio-video device. For example, the broadcast device may be an audio-video screen that displays the personalized message in audio and visual format. In one embodiment, multiple such devices are located throughout the washroom facility and are operatively linked to a common receiver such that the multiple devices display generally the same message. In an alternate embodiment, the washroom facility comprises a plurality of individual functional locations, such as a plurality of toilet stalls or multiple sinks, with each of the functional locations having a respective receiver and associated broadcast device. With this configuration, multiple patrons at the various functional locations may be simultaneously provided with their own personalized message.

In yet another embodiment, the stored files in the processor memory system may also contain preferences of the respective patron with respect to environmental conditions within the washroom facility, such as any one or combination of temperature, lighting, music, or air freshener. The processor system may be in communication with an environmental controller associated with the washroom facility to change the environmental conditions within the facility in accordance with the patron's preferences upon detection of the respective patron within the washroom facility. For example, a patron may have listed a preference for jazz music in their personal profile, and when the patron enters the washroom facility and is detected, the processor system will instruct the environmental controller to change music played in the facility to jazz.

DETAILED DESCRIPTION OF THE INVENTION

Figure 1:
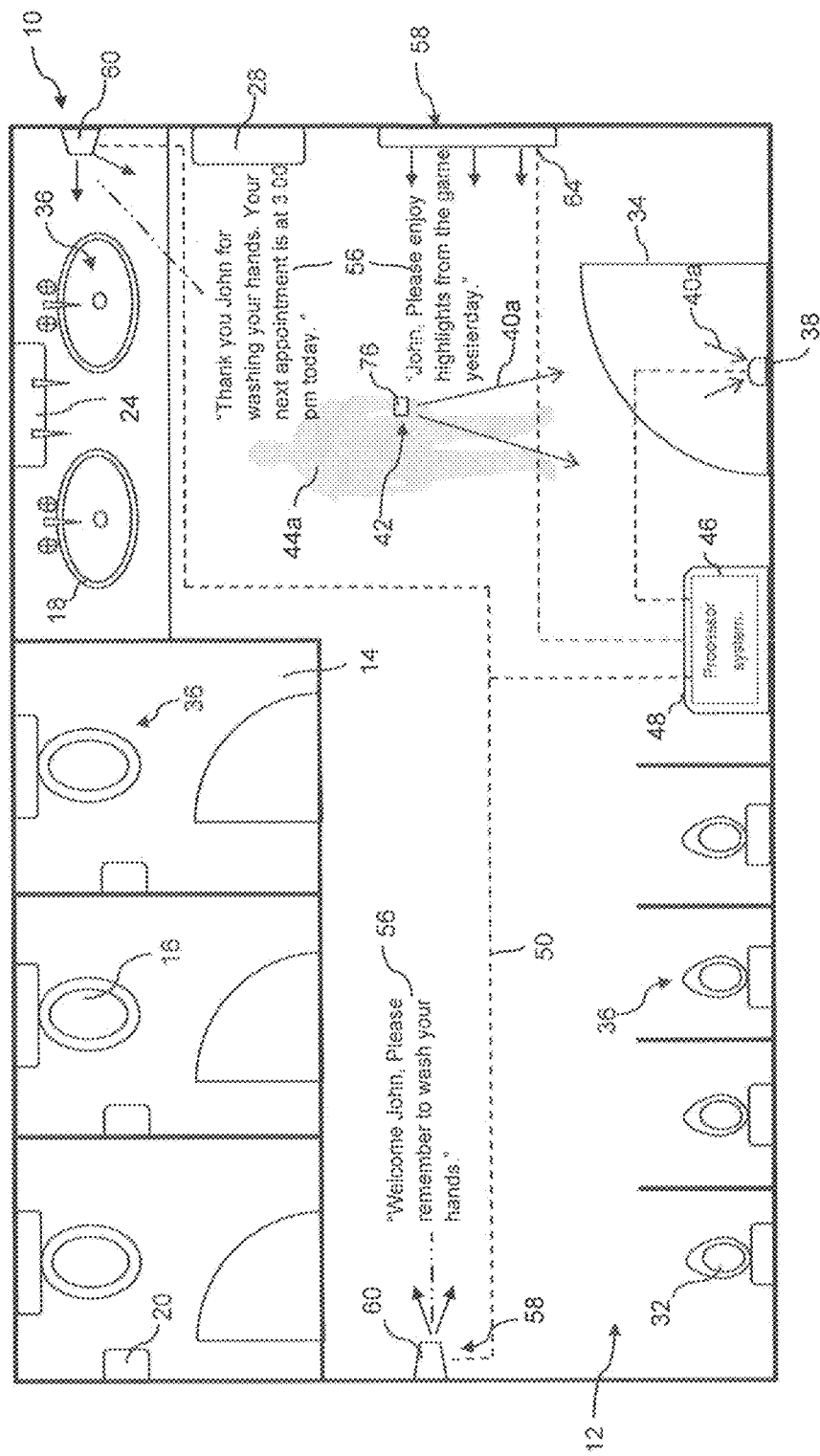
FIG. 1 is a diagram view of a washroom facility incorporating a system that provides a personalized experience to patrons in accordance with aspects of the present invention.

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

As mentioned, the present invention relates generally to a method and system wherein a washroom facility is configured to provide patrons with a personalized washroom experience. Referring to FIG. 1, an embodiment of a system 10 is illustrated as a public or semi-private washroom facility 12 that incorporates certain other aspects of the invention. The design and features of the washroom facility 12 depicted in FIG. 1 is for illustrative purposes only. The washroom facility 12 may be found in an office building, or other away-from-home environment, as discussed above. The washroom facility 12 is depicted as a men's restroom facility having a number of individual urinals 32 and stalls 14, wherein the stalls 14 include individual toilets 16. A number of sinks 18 are also provided. Any combination of other conventional washroom components may also be provided in the washroom facility 12, such as toilet tissue dispensers 20, soap dispenser 24, towel dispenser 28, and so forth. The individual stalls 14, urinals 32, and sinks 18, may be considered as functional locations 36 wherein an individual patron 44a may perform a desired washroom function within the facility 12. It should be appreciated that any manner of additional functional locations 36 may also be included in the washroom facility 12, such as shower stalls, dressing rooms, infant changing stations, and so forth.

Still referring to FIG. 1, the washroom facility 12 is configured with one or more receivers 38 that are located within the facility 12 to detect and receive an active ID signal 40a that is transmitted by a transmitter 42 carried by the patron 44a. In the embodiment illustrated in FIG. 1, the washroom facility 12 includes a single receiver 38 that is positioned above or near the entrance or door 34 to the facility 12. At this location, the receiver 38 detects the individual patron 44a as they enter the facility 12.

The ID signal 40a transmitted by the transmitter 42 is unique to the particular patron 44a. In other words, each patron that enters the facility 12 carries a device 76 that generates a signal 40a that is unique to that particular patron 44a. In this manner, as explained in greater detail below, the system 10 is able to differentiate patrons 44a that enter the facility 12.

Still referring to FIG. 1, the system 10 includes a computer processor system 46 that is in wired or wireless communication with the receivers 38 located within the facility 12. In the embodiment illustrated in FIG. 1, the processor system 46 is located within the facility 12, for example within a control cabinet 48 or other location in the facility 12. The components of the system 10 are, in the illustrated embodiment FIG. 1, in wired communication with the processor system 46 via a wired communication network 50. The processor system 46 includes any manner of hardware and software configuration to carry out the functions described herein. The receiver 38 transmits all or a portion of the received ID signal 40a to the processor system 46, which includes a memory with respective files associated with the unique ID signals 40a. For example, each unique ID signal 40a may have an individual respective file stored in the processor system 46, wherein the system 46 retrieves or opens the stored file associated with the unique ID signal 40a and retrieves personal information stored in the file related to the particular patron 44a. The stored information may include the patron's name, job or position within the company, medical conditions or medications, personal preferences, such as favorite sports teams, favorite music, hobbies, and the like, and so forth. This information may be authorized by the patron via a personal profile questionnaire or other type of submission to the building facilitator or other responsible party. This file information is retrieved by the processor 46 and is used to generate and transmit a personalized message 56 to a broadcast device 58 within the facility 12.

In the embodiment depicted in FIG. 1, a number of broadcast devices 58 are illustrated, including an audio device 60 (e.g. speaker) located adjacent the sinks 18, another audio device 60 located on a wall of the facility 12, and an audio/video (A/V) device 64 located on a front wall of the facility 12, and so forth. All of these devices 58 are in communication with the processor system 46 via the wired communications network 50, as depicted by the dashed lines in FIG. 1, or a suitable wireless communication network.

In FIG. 1, the personalized message 56 broadcast over the audio devices 60 is a greeting that welcomes the patron by name and reminds the patron ("John") to wash their hands upon leaving the facility. The A/V device 64 may play or broadcast the same or a different message. In this particular embodiment, the A/V device 64 also invites the patron by name to watch highlights from a sports game while they are in the facility 12.

In FIG. 1, the single receiver 38 is disposed at or near the door 34 to the facility 12 to initially detect the patron 44a as they enter the facility 12. However, once the patron 44a is within the facility 12, they can move beyond the detection range of the receiver 38. Thus, in this particular embodiment, the system 10 can differentiate patrons 44a as they enter the facility 12, but does not track or otherwise determine the location of the patrons 44a relative to any particular one of the functional locations 36. Thus, this particular embodiment of the system 10 does not generate individual personalized messages 56 at each of the respective functional locations 36. This embodiment may be useful in relatively smaller washroom facilities 12 wherein foot traffic through the facility 12 is at a minimum. With the system of FIG. 1, as additional patrons 44a enter the facility, the same type of messages will be played for each of the individual patrons 44a, with the messages personalized with at least the respective patron's name.

The personalized messages 56 may be broadcast based on a time function. For example, the personalized messages 56 may be repeated for a set period of time in which it is expected that the patron 44a will remain in the facility 12. In another embodiment, the receiver 38 may also be used to detect when the patron 44a exits the washroom facility 12, which then causes the processor system 46a to terminate play of the personalized messages 56.

As discussed with respect to FIG. 1, each of the washroom facilities 12 is equipped with wireless communication capability between the receiver 38 and the transmitter 42 carried by the respective patrons 44a, wherein an intermittently transmitted data packet (i.e., unique ID signal 40a) is transmitted and received within a limited range. In this regard, the washroom facilities 12 are considered to be "communication-enabled" facilities. It has been found that Bluetooth Low Energy (BTLE) technology is particularly well-suited for purposes of systems 10 in accordance with the present subject matter. For example, the transmitter devices 42 carried by the patrons 44a may be BTLE beacons 76 that transmit the unique ID signal 40a as a BTE formatted signal, and the receiver 38 is a BTLE scanner configured to receive and recognize the BTLE formatted signal 40a.

BTLE beacons are commercially available and are relatively small devices that can be disguised as a "trinket" that is worn or carried by the patron 44a. For example, the BTLE beacon 76 may be a bracelet (e.g., similar to a medical alert bracelet), a component of an identification badge worn by company employees, a decorative or functional item attached to a patron's belt or clothes, and so forth.

BTLE devices are well-known to those skilled in the art, and a detailed explanation of their function and operation is not necessary for an understanding and appreciation of the present invention. Briefly, BTLE beacons are a class of low-energy, low-cost radio transmitters that can a receiver running BTLE applications of their presence, which in turn enables the receiver to perform certain actions when in close proximity to the beacon. These devices are often referred to as "iBeacons", which is the name Apple chose for its implementation of the BTLE technology. Each BTLE beacon broadcasts a unique identification signal using the BTLE standard format. These unique signals are also known as iBeacon "advertisements." The BTLE receiver runs an application that enables the device to scan for and receive the signals within transmitting range of the BTLE beacons. The receiver will automatically "react" to the received signal and may start other BTLE-enabled applications for various purposes, including communication with a central server, which in this case is the processor system 46.

A typical use of BTLE technology is relatively precise indoor geo-location ("micro-location"). A BTLE-enabled application on receiver is notified when the BTLE beacon (transmitter 42) moves out of range of the receiver, and thus is able to determine distance of the transmitter 42 (and patron 44a) from the receiver 38. The exact geo-location of the receiver 38 is known, and thus the exact location of the transmitter 42 (and patron 44a) is calculated based on relative distance from the receiver 38 as a function of signal strength. With this location information, the processor system 46 in communication with the receiver 38 can generate a personalized message 56 to the patron 44a telling them, for example, that a nearby functional location 36 in the facility 12 is out-of-order or occupied, and so forth.

Figure 2:
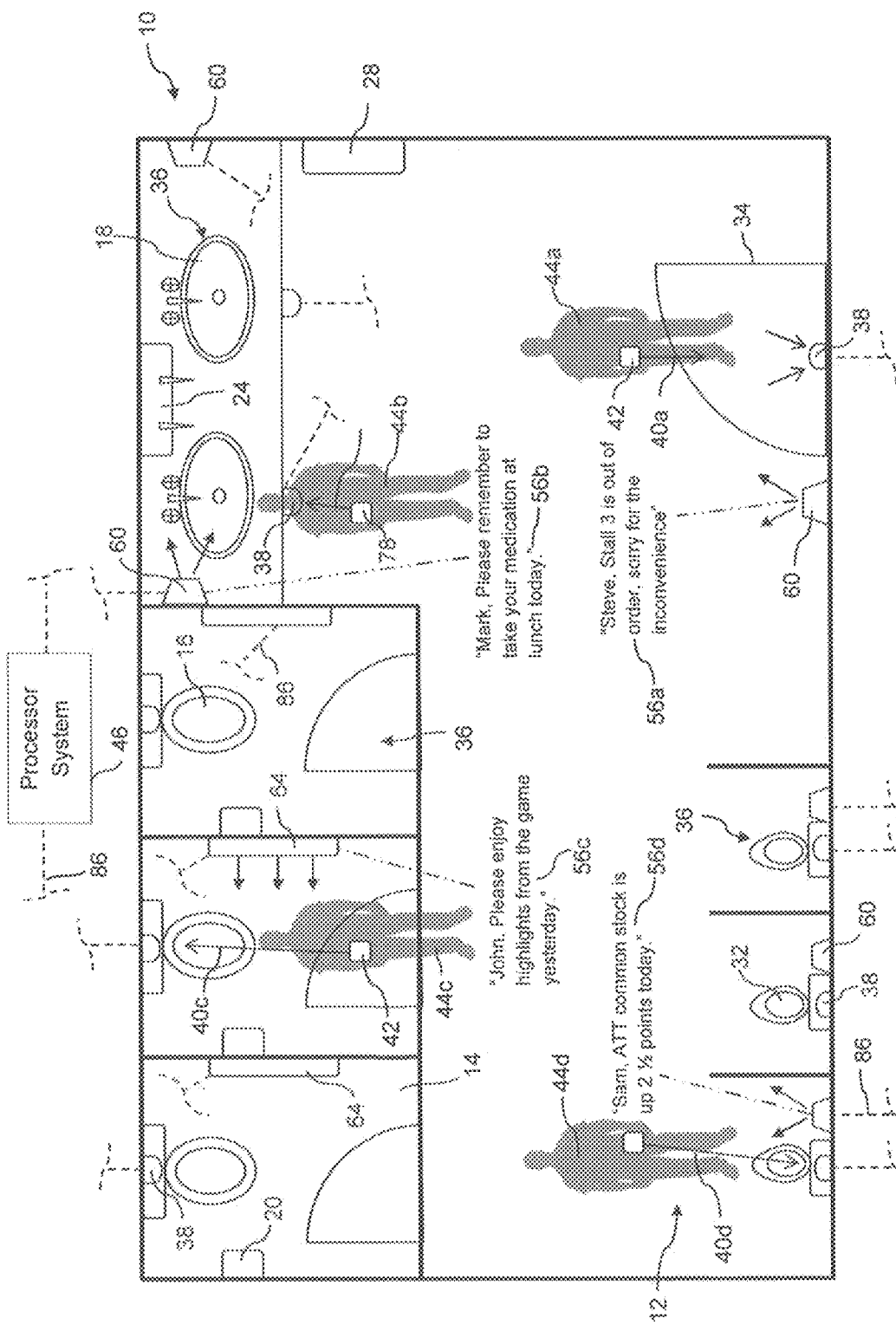
FIG. 2 is a diagram view of a washroom facility incorporating an alternate embodiment of the system for providing a personalized experience to patrons.

In certain embodiments, the BTLE beacon function may be incorporated with a patron's mobile smart device. In the embodiment of FIG. 2, for example, the patron 44b has on their person a mobile smart device 78, such as a smart phone, tablet, PDA, or other network-enabled device (all referred to herein generically as a "mobile smart device"). The mobile smart device 78 runs a low-power background application previously downloaded by the player 16 from a source (e.g. a website) that allows the mobile smart device 78 to function as a BTE beacon that intermittently transmits the unique BTLE signal 40B during certain times of the day, for example during normal working hours, or other times programmed by the patron 44b.

It should be appreciated that the present systems and methods are not limited to BTLE technology. Other transmitter/receiver technologies may also be utilized for practice of the invention. For example, Near Field Communication (NFC) implementations may be utilized. In another embodiment, Radio Frequency Identification (RFID) technology may be used. Other communication technologies are also within the scope and spirit of the invention.

FIG. 2 illustrates another embodiment of a system 10 in accordance with aspects of the invention. In this embodiment, the processor system 46 is remote from the washroom facility 12, and may be located in a different location within the same building, or a different building altogether. The processor system 46 is in wireless communication with the various components of the system 10 via any manner of suitable wireless 86 wide area network (WAN) or local area network (LAN) communications network. Such networks are well known to those skilled in communication systems, and a detailed explanation of a suitable wireless network 86 is not necessary for purposes of an appreciation of the present invention.

FIG. 2 differs from the embodiment of FIG. 1 in that a plurality of the receivers 38 are located throughout the washroom facility 12. In addition to the receiver 38 at or near the door 34, an individual respective receiver 38 is associated with the individual functional locations 36. For example, an individual receiver 38 is associated with each sink 18, with each toilet facility 16 located in each individual stall 14, and with each urinal 32. Thus, with this embodiment, a number of different patrons 44a, 44b, 44c, and 44d within the washroom facility 12 using different ones of the functional locations 36 are individually detected by a respective receiver 38. In addition, each of the functional locations 36 is configured with a respective broadcast device 58 so that the respective patron utilizing the individual functional location 36 can receive a personalized message 56 via the broadcast device 58 associated with their respective functional location 36. For example, patron 44b at one of the sink locations 18 emits a unique ID signal 40b from his transmitter 42 carried by the patron 44b, which in this case is the patron's mobile smart device 78. The unique ID signal 40b is detected by the receiver 38 located in front of the sink 18, and the receiver 38 transmits all or a portion of the unique ID signal 40b to the processor system 46 via the wireless communication system 86. The processor system 46 then generates a personalized message that is broadcast to the patron 44b via the audio device 60 located adjacent to the sink 18. For example, in this instance, the personalized message 56b reminds the patron ("Mark") to take his medication at lunch. The processor system 46 retrieved the medication information necessary to generate the message 56b from the stored file associated with the unique ID signal 40b.

The patron 44a in FIG. 2 has just entered the facility 12 and his unique ID signal 40a is detected by the receiver 38 located at or near the door 34. The processor system 46 generates a personalized message 56a that is broadcast to the patron 44a via the audio device 60 located near the door 34, wherein the patron ("Steve") is informed that "stall 3" in the facility 12 is out of order.

The patron 44c in the middle stall 14 transmits a unique ID signal 40c that is received by the receiver 38 located within the stall. Each of the stalls 14 may be equipped with an A/V device that broadcasts both video and sound recordings to the patrons. In this example, the patron 44c ("John") is invited by name to view highlights from a sports game on the AN device 64. The particular sports team or highlights chosen for the broadcast are personalized for the patron based on a preference profile stored for the particular unique ID signal 40c.

The patron 44d in FIG. 2 is at one of the urinals 32 wherein his unique ID signal 42 is received by a receiver 38 located above the respective urinal. The processor system 46 generates a personalized message 56d to the patron 44d reporting the price of a particular stock to the patron via the audio device 60 located at the urinal 32. The stock quote may be personalized in that the processor system 46 retrieves one or more stocks of interest to the patron 44d from the file associated with the unique ID signal 40d and generates the message 56d with a current stock price.

It should be appreciated that the embodiment in FIG. 2 is particularly useful in that a number of patrons 44a through 44d are individually provided with personalized messages 56a through 56d simultaneously while they are all within the facility 12.

Figure 3:
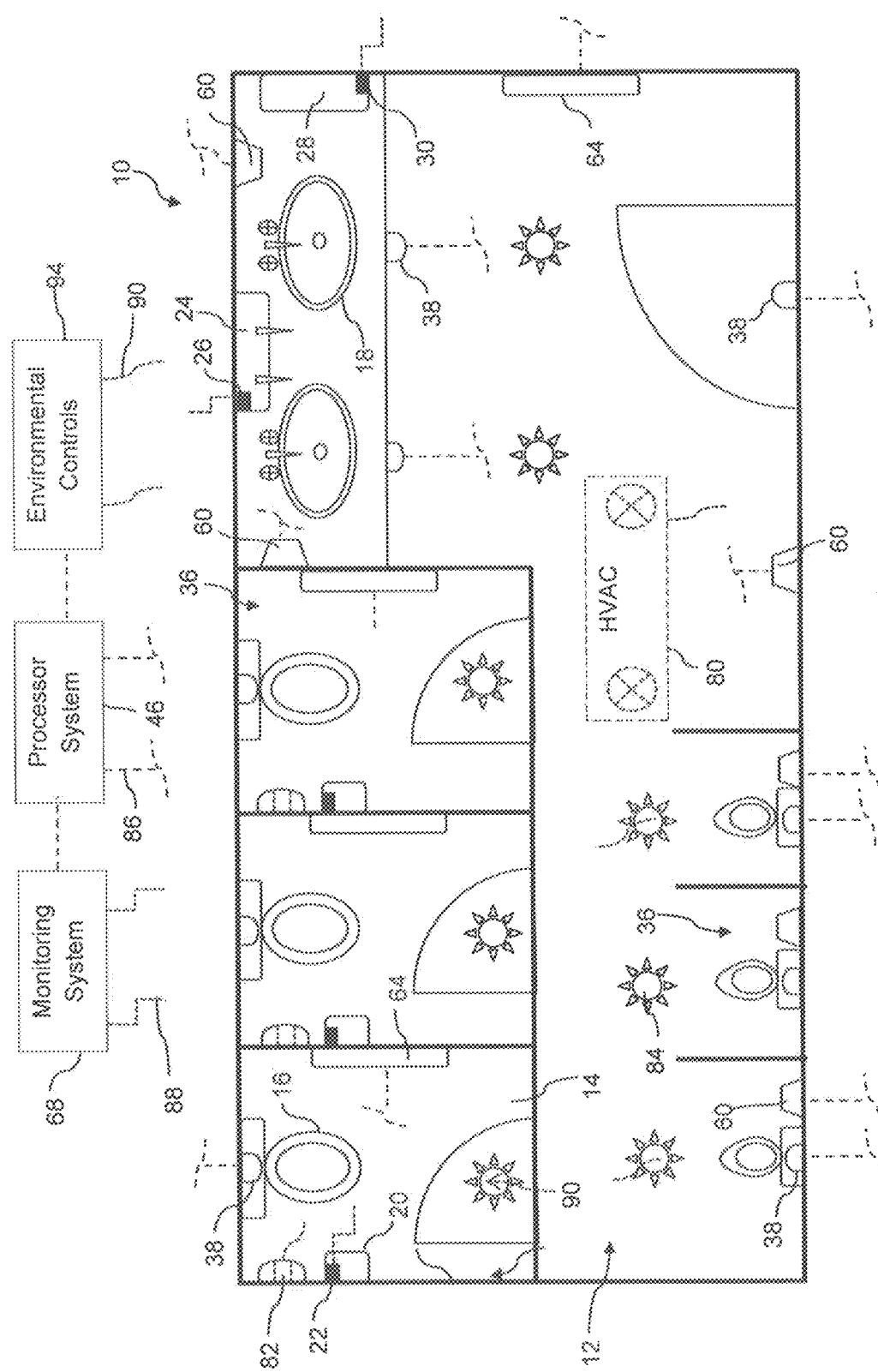
FIG. 3 is a diagram view of a washroom facility incorporating yet another embodiment of the system for providing a personalized experience to patrons.

FIG. 3 depicts an embodiment wherein the system 10 is incorporated with a "smart" washroom facility 12. With this type of facility, the consumable product dispensers, such as the paper towel dispenser 28, toilet tissue dispensers 20, and soap dispenser 24, are equipped with respective sensors 30, 22, and 26 that detect the amount of product usage, and thus the remaining amount of product in the respective dispenser. Dispensers of this type are known in the art. The dispensers 20, 24, 28 are in communication with a monitoring system 68 via any manner of suitable wireless communication 84. Typically, the monitoring system 68 is a computer-implemented system remotely located from the washroom facility 12. The monitoring system 68 may monitor a number of similarly-configured washroom facilities 12 within a building, such as an office building. With this particular system, the processor system 46 is also in communication with the monitoring system and, thus, can receive information regarding product usage or availability in any one of the dispensers located at one of the functional locations 36. In this regard, one of the personalized messages 56 that may be generated for a patron at one of the functional locations 36 may relate to the remaining amount of product within a dispenser. For example, a patron about to enter one of the stalls 14 may receive a personalized message that informs the patron by name that the toilet tissue dispenser 20 has a limited amount of toilet tissue remaining, and encourage the patron to visit one of the other stalls. It should be appreciated that any information generated by the monitoring system 68 regarding a component within the washroom facility 12 may be used to generate a personalized message by the processor system 46 that is of relevant interest to an individual patron.

FIG. 3 also depicts that the washroom facility 12 has a number of environmental components, such as an HVAC system 80, individually controllable lights 84, individual air fresheners 82 within each of the stalls 14, and so forth. These environmental components are in communication with an environmental controls system 94 through any suitable wireless communication network 90. The controls system 94 may be integrated with the monitoring system 86. The processor 46 may also be in communication with the environmental controls system 94, and may function with the system 94 to individually or collectively control various ones of the environmental components to further provide a personalized washroom experience to an individual patron. For example, the stored file for a unique ID signal associated with a patron may include patron preferences with respect to ambient conditions, such as temperature, music, lighting, a particular type of air freshener, and so forth. The processor system 46 may access this information and communicate with the environmental control system 94 to change the ambient environmental conditions within the washroom facility 12 in accordance with a particular patron's preference. For example, the processor system 46 may initiate changes within the individual stall 14 to change the lighting conditions within the stall 14, music played in the stall 14 via a central music system controlled by the environmental control system 94, or to disperse any one of a number of different scents from an air freshener 82 that is equipped with a plurality of different air freshening substances.

Figure 4:
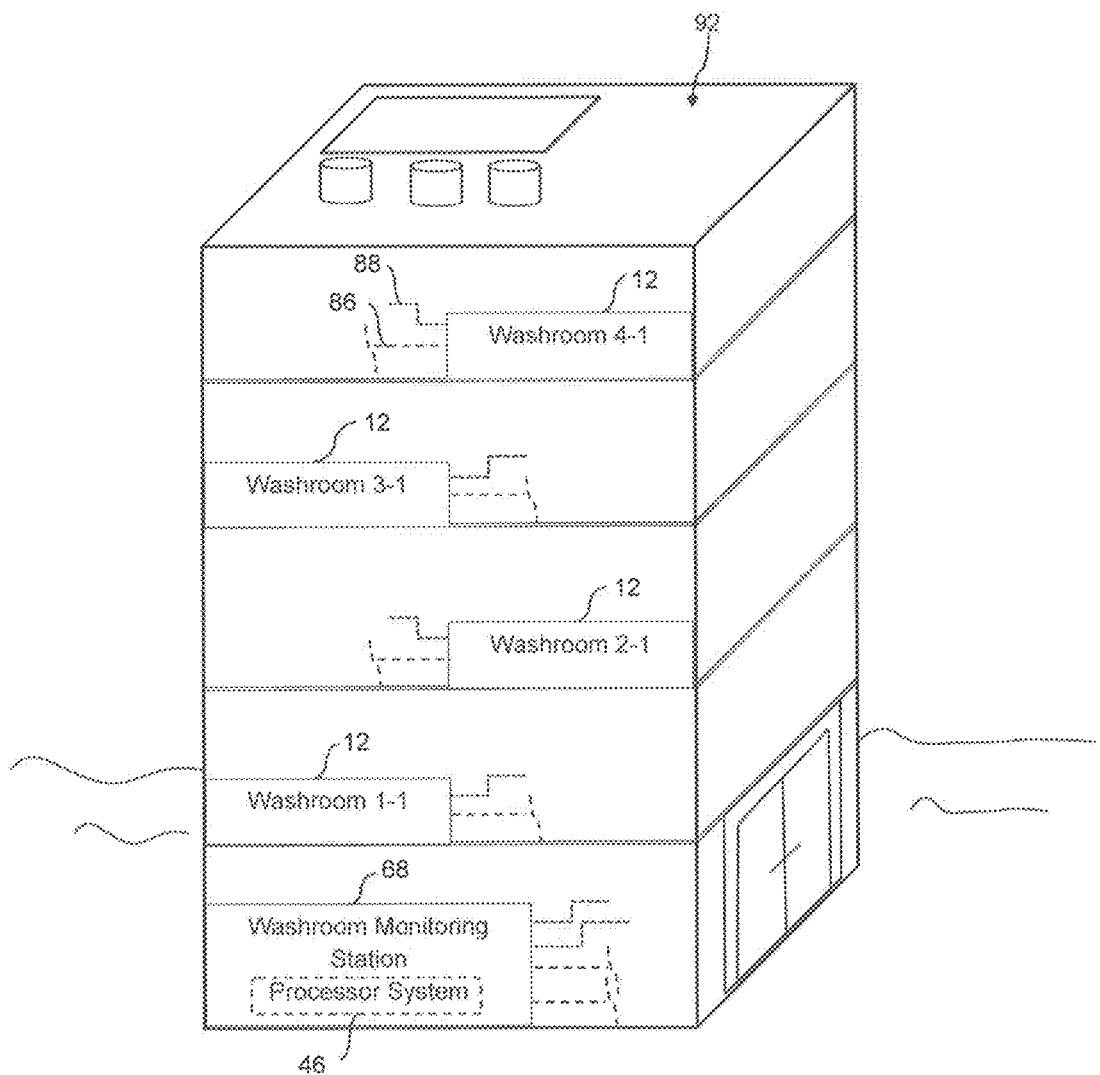
FIG. 4 is a is a diagram of a multi-floor building with a washroom on each floor that incorporates a system in accordance with aspects of the invention.

FIG. 4 depicts a building 92, such as a conventional office building having multiple floors. At least one washroom facility 12 configured in accordance with the invention is provided on each of the floors. A remote processor system 46 is located with a remote washroom monitoring station 68, for example in a bottom floor or other maintenance location, and is common to the plurality of facilities 12. The present washroom system 10 is particularly useful in such a building 92 wherein the patrons visiting the washroom facilities 12 are known and can be readily provided with a suitable transmitter 42 having a unique ID signal associated with the individual respective patron. The processor system 46 may be maintained or managed by a central authority, such as the maintenance company responsible for the building 92. Employees with each of the different companies or businesses located on the different respective floors are provided with the opportunity to submit preference profiles and other personal information stored in the respective files maintained by the processor system 46 so that such employees can be provided with the personalized messages and washroom experience as discussed herein.

Thus, certain embodiments will have multiple washroom facilities 12 within a single building or multiple building linked to one or more central processor systems 46 and one or more monitoring systems 86, with each dispenser within the multiple of washroom facilities 12 in communication with the systems 46, 86. In this regard, a communications network is configured for these functions, wherein the individual dispensers are considered as network-enabled devices that may be directly connected to the network through a plurality of direct network links, thereby eliminating the need for the bus, router, or other networking equipment. It should also be appreciated that each of the network enabled devices (or a group of such devices) in this configuration may represent a node that, in turn, may be directly connected and/or multiplexed to the network via the direct network links. Further, the direct network links may represent secure communications channels physically hardened against tampering and/or the communications may be encrypted to prevent unauthorized access to information transmitted thereon.

The central processor system 46 (which may be integrated with a building monitoring system 68 as discussed above) may include a host computer, which may be an integrated server, or include any manner of periphery server or other hardware structure. The central processor system 46 may be a single networked computer, or a series of interconnected computers having access to the network via a gateway or other known networking system. Generally, the central processor system 46 may include a central controller configured to manage, execute and control the individual terminal dispenser units, and to interface with the network enabled broadcast devices for retrieval/generation and play of the personalized messages described herein. The central controller may include a memory for storing gaming procedures and routines, a microprocessor (MP) for executing the stored programs, a random access memory (RAM) and an input/output (I/O) bus. These devices may be multiplexed together via a common bus, or may each be directly connected via dedicated communications lines, depending on the needs of the system 100.

The central controller may be directly or indirectly connected through the I/O bus to any manner of peripheral devices such as storage devices, wireless adaptors, printers, and the like. In addition, a database (DB) may be communicatively connected to the central controller and provide a data repository for the storage and correlation of information gathered from the individual dispenser units, display devices 58, or nodes of such devices.

It should be appreciated that the network-enabled devices (e.g., the individual dispenser units and/or display devices) may include similar features or may be configured with functionality to allow for an exchange of information required to function as described herein. The network-enabled devices may include a number of internal components, such as a controller having a program memory, a microcontroller or microprocessor (MP), a random access memory (RAM), and an input/output (I/O) bus, all of which may be interconnected via an address or data bus. The controller may include multiple, and even redundant, program memories and random access memories to increase expandability, capacity and/or processing speed.

The program memory and random access memory may be implemented as a solid-state memory, an integrated circuit, a magnetically readable memory, and/or optically readable memories. Further, the program memory may be read only memory (ROM) or may be read/write memory such as a hard disk. In the event that a hard disk is used as the program memory, the data bus may comprise multiple address/data buses, which may be of differing types, and there may be a separate I/O circuit between the data buses.

Network-enabled devices may be distributed throughout a single establishment and connected with a LAN, or throughout multiple sites and connected with a WAN. Further, the LAN and/or WAN connecting each of the devices may include one or more separate and secure buses, routers, web servers, gateways and other networking equipment to provide continuous and/or redundant connectivity to the network.

Figure 5:
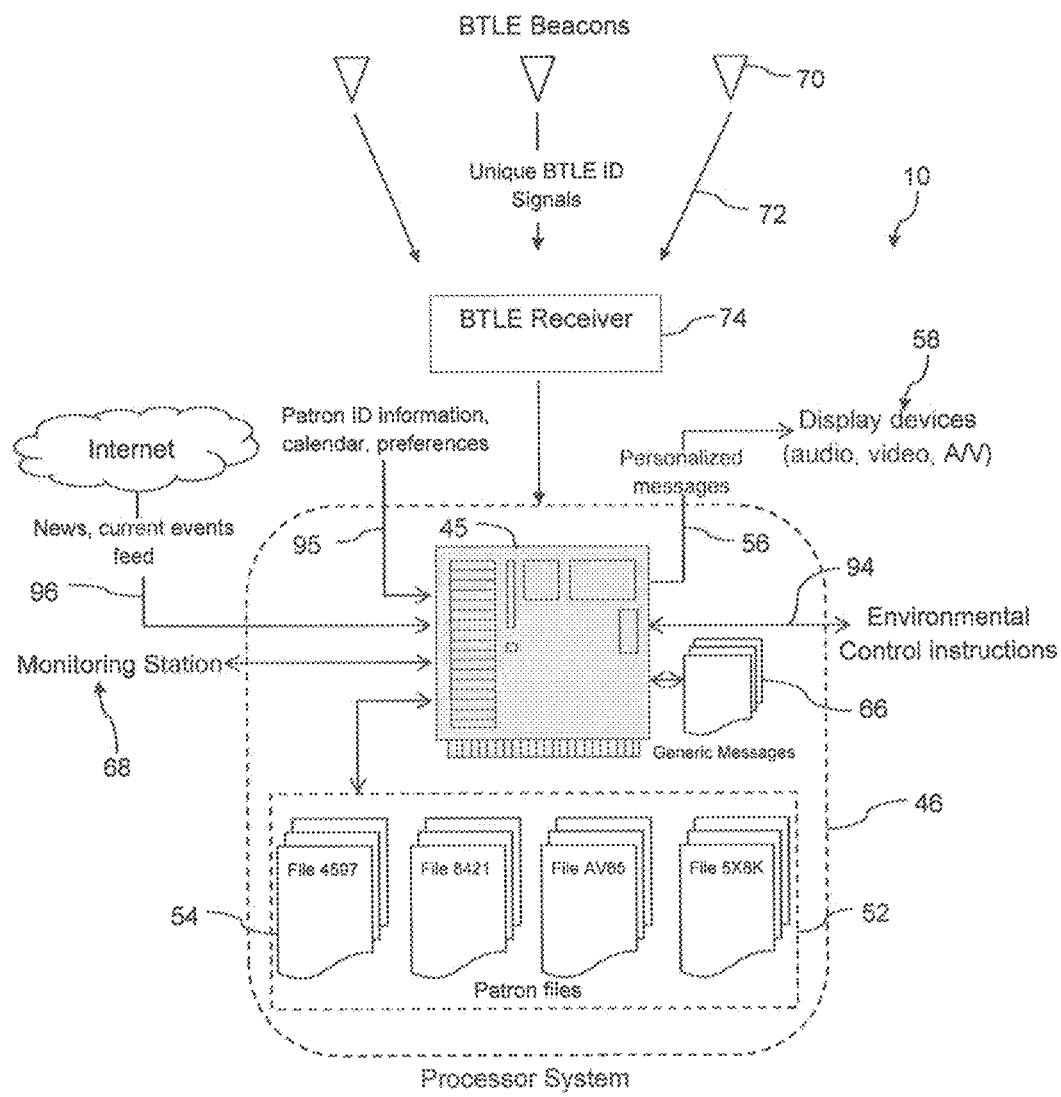
FIG. 5 is a component diagram view of certain control features of a system in accordance with the invention.

FIG. 5 is a schematic illustration of certain control aspects of a system 10 in accordance with the invention. In this particular system 10, the processor system 46 includes any manner of computer-implemented server 45. The system 46 includes a library 52 in which the individual patron files 54 are stored. Each file 54 is associated with a unique BTLE signal 72 generated by a BTLE beacon 70. As discussed above, the BTLE beacons 70 are an embodiment of a transmitter 42 carried by the respective patrons that visit a washroom facility 12 equipped with the system 10. The unique BTLE signals 72 are received by a BTLE enabled receiver 74 located within the washroom facility 12. As discussed above, a single receiver 74 may be associated with each washroom facility 12, or a plurality of different receivers 74 may be located throughout the facility 12, for example at each of the individual functional locations 36 within the facility 12.

Still referring to FIG. 5, the BTLE receiver 74 transmits all or a portion of the signals 72 to the processor system 46, which retrieves the related patron files and generates the personalized messages 56.

FIG. 5 depicts a number of inputs to the processor system 46 that enable different types of personalized messages 56 to be generated and broadcast to the patrons. For example, one of the inputs labeled "patron ID information, calendar, preferences" is the input that enables the individual employees or patrons of the washroom facility 12 to enter their personal preferences. This input also indicates that the processor system 46 may be electronically linked to an electronic calendar for each of the respective patrons. In this manner, referring to FIG. 1, one of the personalized messages 56 generated and broadcast to the patron may inform the patron of an upcoming event on their calendar.

Another input 96 to the processor system 46 depicts that the system 10 may be in communication via the internet for any other wide-area network with a service that provides news or other current events information. In this manner, one of the personalized messages 56 generated for a particular patron may relate to news, sports, financial, or other subjects that are of interest to the patron and referenced in the patron's personal profile stored in the respective files 54.

The communication link 68 relates to the functionalities associated with a smart washroom monitoring station as discussed above with respect FIG. 3, as well as the environmental control functionalities 94 also discussed above with respect to FIG. 3.

FIG. 5 also depicts a library 66 of generic messages that are not yet personalized for an individual patron. For example, such messages may simply be greetings, such as "Good afternoon _____" or "Have a nice day _____". The system 46 may retrieve any one or combination of these generic messages 66 and then use personal information obtained from the patron files 54 to populate the generic messages 66, thereby transforming the generic messages 66 into personalized messages.

The library 66 of generic messages may convey general health or well-being information and suggestions to the patrons. For example, such message may encourage the patron by name to exercise at least one-half hour that day, or inform the patron of exercise class schedules at an on-site facility. The type of health information that may be conveyed to the patrons is vast.

While the present invention has been described in connection with certain preferred embodiments it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. A washroom system wherein patrons receive personalized messages, comprising:
   a washroom facility configured with a receiver that receives a respective ID signal unique to particular patrons that enter the washroom facility;
   an ID signal transmitter carried by the patrons, each of the ID signal transmitters generating the ID signal unique to the respective patron;
   a processor system in communication with the receiver, wherein the receiver transmits the unique ID signals to the processor system, the processor system remote from the washroom facility and common to a plurality of different washroom facilities;
   the processor system comprising a memory with files associated with each of the unique ID signals, the files containing information on the patron associated with the unique ID signal that is retrieved by the processor upon receipt of the unique ID signal from the receiver, the processor using the personal information to generate and transmit the personalized message to a broadcast device in the washroom facility; and
   wherein the personalized messages greet the respective patron by name and provide additional information or instruction to the patron.

2. The washroom system as in claim 1, wherein the files contain personal preferences of the respective patron that are unrelated to activities performed by the patron in the washroom facility, and the additional information or instruction relates to subject matter of preferences.

3. The washroom system as in claim 1, wherein the files contain medical information of the respective patron, and the additional information or instruction relates to the medical information.

4. The washroom system as in claim 1, wherein the processor system is linked to an electronic calendar for the respective patron, and the additional information or instruction relates to upcoming events on the patron's calendar.

5. The washroom system as in claim 1, wherein the processor system comprises a library of generic messages and retrieves and personalizes one of the generic messages with the information unique to the respective patron to generate the personalized message to the patron.

6. The washroom system as in claim 1, wherein the additional information or instruction relates to status or availability of functional locations within the washroom facility.

7. The washroom system as in claim 1, further comprising a remote washroom monitoring station within a common building as the washroom facility, the processor system located at the washroom monitoring station, the processor system being common to a plurality of similarly configured washroom facilities within the building.

8. The washroom system as in claim 1, wherein the ID single transmitter is a Bluetooth Low Energy (BTLE) beacon that emits a unique BTLE ID signal for each respective patron, the receiver comprising a BTLE-enabled receiver that receives and transmits all or a portion of the unique BTLE ID signals to the processor system to enable retrieval of one or more of the personalized messages for playback to the patron.

9. The washroom system as in claim 8, wherein the BTLE beacon is incorporated with a trinket provided to the patrons.

10. The washroom system as in claim 8, wherein the BTLE beacon is incorporated with a mobile smart device carried by the patron, the mobile smart device having an application that causes the mobile smart device to transmit the unique BTLE ID signal.

11. The washroom system as in claim 1, wherein the broadcast device is any one or combination of an audio device, video device, or audio-video device.

12. The washroom system as in claim 11, wherein the washroom facility comprises a plurality of individual functional locations, each of the functional locations having one of the receivers and broadcast devices associated therewith such that multiple patrons at the various functional locations are simultaneously provided with the personalized messages.

13. The washroom system as in claim 1, wherein the files contain preferences of the respective patron with respect to environmental conditions within the washroom facility, the processor system in communication with an environmental controller to change the environmental conditions within the washroom facility in accordance with the patron's preferences upon detection of the respective patron within the washroom facility.

14. The washroom system as in claim 13, wherein the environmental conditions are any one or combination of temperature, lighting, music, or air freshener.

* * * * *